(12) United States Patent
Becker et al.

(10) Patent No.: US 7,476,543 B2
(45) Date of Patent: Jan. 13, 2009

(54) DEVICE AND METHOD FOR WETTING OBJECTS

(75) Inventors: Horst Dieter Becker, Tübingen (DE); Xaver Einsle, Stuttgart (DE)

(73) Assignee: Texogene International GmbH, Jena (DE)

( * ) Notice: Subject to any disclaimer, the term of this patent is extended or adjusted under 35 U.S.C. 154(b) by 421 days.

(21) Appl. No.: 10/512,355

(22) PCT Filed: Apr. 23, 2003

(86) PCT No.: PCT/EP03/04192

§ 371 (c)(1),
(2), (4) Date: Jul. 7, 2005

(87) PCT Pub. No.: WO03/091705

PCT Pub. Date: Nov. 6, 2003

(65) Prior Publication Data

US 2006/0239858 A1 Oct. 26, 2006

(30) Foreign Application Priority Data

Apr. 24, 2002 (DE) ................... 102 18 988

(51) Int. Cl.
*G01N 1/28* (2006.01)
*G01N 1/31* (2006.01)
*B01L 3/00* (2006.01)
*C12M 1/00* (2006.01)

(52) U.S. Cl. ............... 436/43; 422/100; 435/303.1

(58) Field of Classification Search .............. 436/43; 422/100; 435/40.5, 40.52, 287.2, 303.1; 118/401; 702/19

See application file for complete search history.

(56) References Cited

U.S. PATENT DOCUMENTS

| 3,667,896 A | 6/1972 | Johnson |
| 3,853,092 A | 12/1974 | Amos et al. |
| 4,335,673 A | 6/1982 | Fixot |
| 4,651,671 A | 3/1987 | Pedersen |
| 5,068,091 A | 11/1991 | Toya |
| 5,338,358 A | 8/1994 | Mizusawa et al. |
| 5,654,200 A | 8/1997 | Copeland et al. |
| 5,681,741 A * | 10/1997 | Atwood et al. ........... 435/287.2 |

FOREIGN PATENT DOCUMENTS

| DE | 39 05 465 | 8/1989 |
| DE | 42 33 794 | 10/1993 |
| DE | 199 49 735 | 5/2001 |

(Continued)

OTHER PUBLICATIONS

Nordhoff, Eckehard, Processing of Samples with a Defined Small Wall Contact Surface, May 2001. (Machine Translation of DE 199 49 735 A1).*

*Primary Examiner*—Walter D Griffin
*Assistant Examiner*—Christine T Mui
(74) *Attorney, Agent, or Firm*—Harness, Dickey & Pierce P.L.C.

(57) ABSTRACT

The invention relates to a device and a method for moistening objects with a liquid by means of a system (1) for carrying a specimen slide that is disposed at a distance from a platform (7). To reduce liquid consumption, the specimen slide is raised or lowered relative to the platform (7) by means of a system (44).

28 Claims, 9 Drawing Sheets

FOREIGN PATENT DOCUMENTS

| | | |
|---|---|---|
| DE | 100 04 802 | 8/2001 |
| EP | 0 961 110 | 12/1999 |
| FR | 2 426 254 | 12/1979 |
| GB | 2 216 261 A | 2/1989 |
| GB | 2 265 981 A | 9/1992 |
| WO | WO 01 51909 | 7/2001 |
| WO | WO 03/091705 A1 | 11/2003 |

* cited by examiner

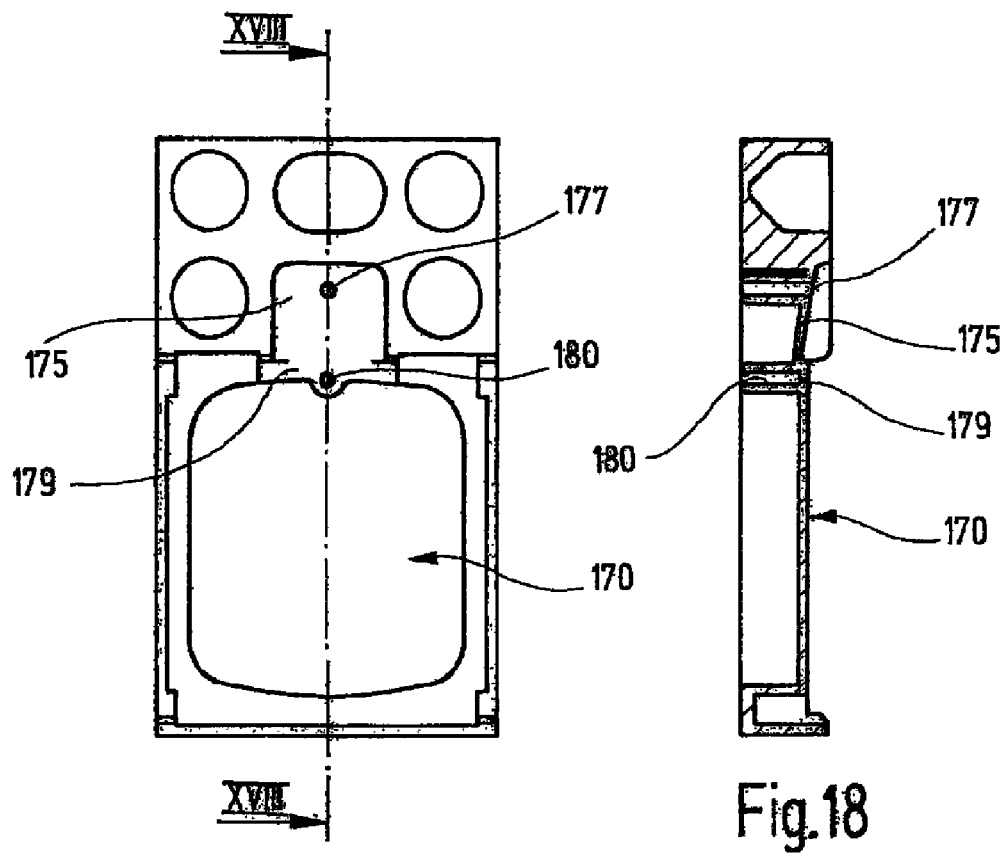
Fig.17
Fig.18
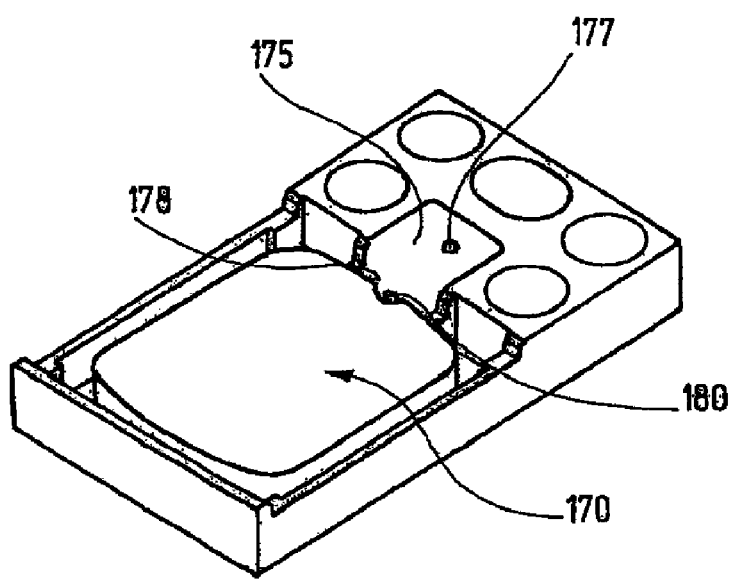
Fig.19

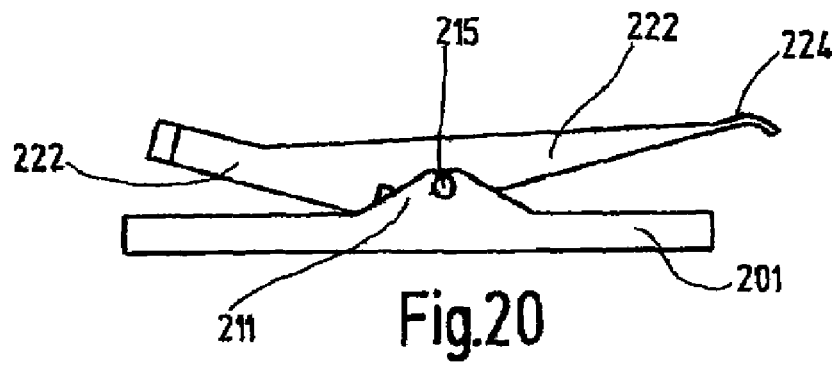
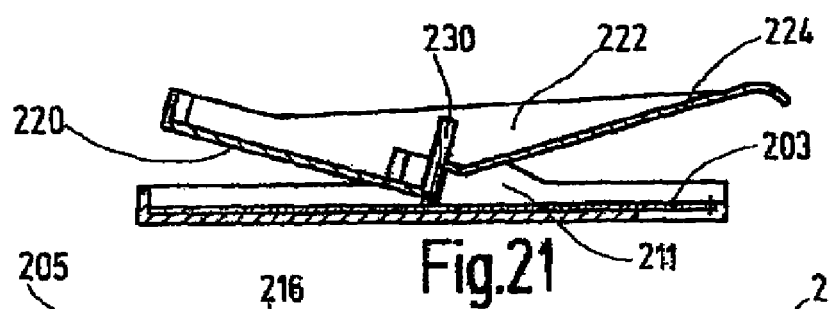
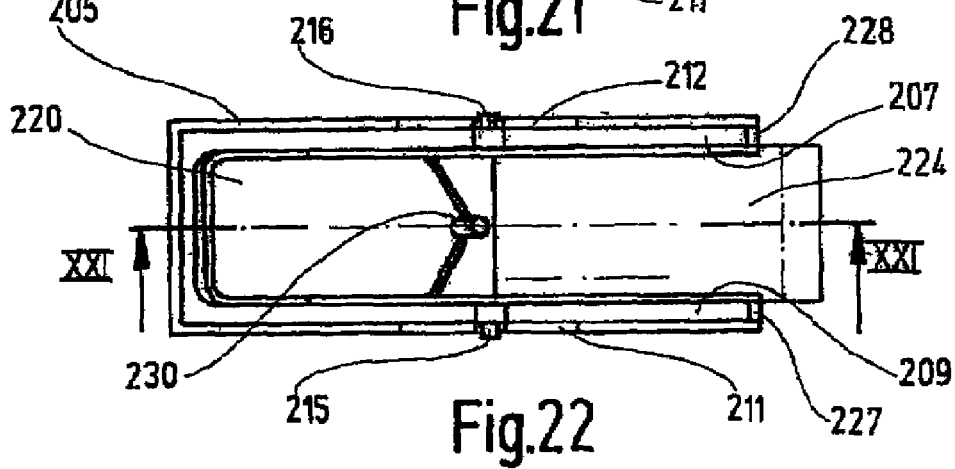
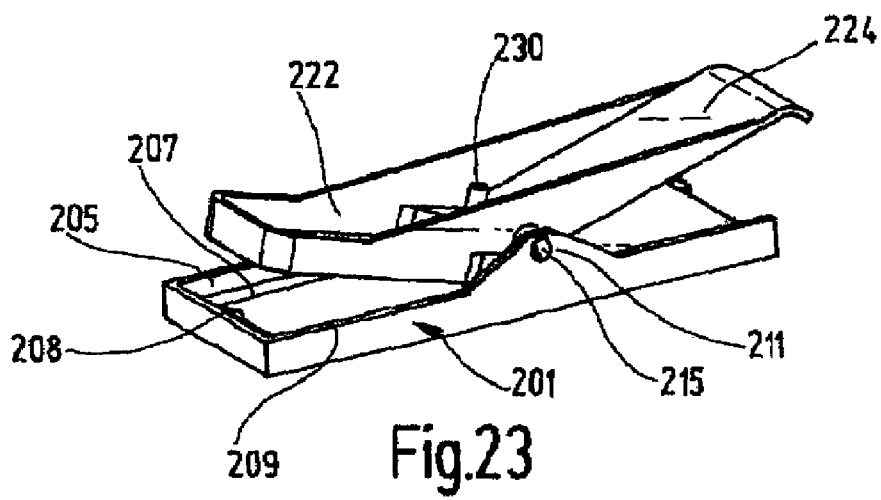

DEVICE AND METHOD FOR WETTING OBJECTS

CROSS-REFERENCE TO RELATED APPLICATIONS

This application is a U.S. National Stage of International Application No. PCT/EPO3/04192 filed 23 Apr. 2003 (23.04.2003). This application claims the benefit of German Application No. 102 18 988.9, filed 24 Apr. 2002 (24.04.2002). The disclosure of the above application is incorporated herein by reference.

The invention refers to a device and a method for wetting objects, particularly materials, with a liquid that may contain an analytical reagent or a substance to be isolated, by use of a system for carrying a specimen slide that is disposed at a distance from a platform.

The device can be used for detection, for example by use of staining, hybridization, nucleic acid-protein binding or protein-protein binding methods, as well as for the isolation of structures and/or constituents of biological materials.

According to a variant of the invention, materials, particularly biological materials, for example tissue samples, cells, cell extracts, nucleic acids such as DNA, RNA, or oligonucleotides, proteins including peptides, haptens, antigens, antibodies or fragments thereof, are applied in punctiform manner or in the form of arrays to the underside of the specimen slide. According to the invention, biochips containing the aforementioned biological materials in fixed form can also be applied.

The underside of the specimen slide with the materials is disposed at a slight distance from the platform. The interspace formed between the underside of the specimen slide and the platform is intended to take in a liquid containing one or more agents for the detection of the materials applied to the specimen slide, or containing substances that are to be isolated by use of the materials applied to the specimen slide.

If, for example, biological materials such as cells or tissue samples are placed on the specimen slide, the liquid can, for example, contain stains to stain and thus detect specific cell constituents or cell structures. The liquid, can, however, also contain nucleic acids such as DNA, RNA or oligonucleotides that are preferably labeled in an appropriate manner and that, after being brought in contact with the cells or tissue samples present on the specimen slide under hybridization conditions, bond to complementary nucleic acids in the cells or tissue samples thus making their specific detection possible. The device of the invention can also be used for in-situ hybridizations. The liquid can also contain, preferably labeled, antibodies or suitable fragments thereof which make possible specific detection of proteins in the cells or tissue samples.

If nucleic acids such as RNA or DNA are applied to the underside of the specimen slide, the liquid can contain, preferably labeled, oligonucleotides, RNA or DNA which under hybridization conditions hybridize with complementary nucleic acids on the specimen slide thus making their detection possible The liquid, however, can also contain proteins. For example, if DNA-binding proteins are involved, they can, after bonding to one or more nucleic acids, particularly DNA, present on the specimen slide, be isolated from the liquid.

If proteins and/or peptides are applied to the underside of the specimen slide, the liquid can, for example, contain antibodies permitting a specific identification of proteins. The liquid, however, can also contain proteins or peptides, particularly those capable of bonding to other proteins. In this case, it is possible, on the one hand, to isolate specific proteins from the liquid because they bind to appropriate proteins on the specimen slide. On the other hand, it is possible in this manner to identify proteins on the specimen slide, particularly if the proteins or peptides present in the liquid are suitably labeled.

By applying antibodies to the underside of the specimen slide, antigens present in the liquid can be isolated.

The object of the invention is to provide a device and a method whereby liquid consumption compared to that occurring in common devices and by use of common methods is reduced. In particular, the invention makes it possible to fill completely and in bubble-free fashion as well as to empty the interspace between the platform and the underside of the specimen slide for both automated and semi-automated as well as manual applications.

A preferred embodiment of the device is characterized by a support system on which the specimen slide, when it is raised and lowered, rests with one side or one corner, the opposite side or corner of the specimen slide resting on the system for raising and lowering the specimen slide. In this manner, a movable tilting arrangement is created which permits reversible swiveling of the specimen slide about one of its sides or about a straight line passing through one of its corners. The mobile tilting device for raising and lowering the specimen slide ensures very low liquid requirements, which has a particularly positive effect on the use of the expensive reagents. The supporting system and the device for raising and lowering the specimen slide should preferably engage in the marginal region of the specimen slide to avoid damaging the tissue on the underside of the specimen slide when the device is in operation. The specimen slide can be made to swivel about its short as well as its long sides. The raising and lowering system can be driven and actuated mechanically, electromagnetically, electrically, pneumatically or hydraulically. In particular, the raising and lowering can be controlled by cams, with the aid of springs or with an inclined plane. For manual use, cam and rotation systems and an inclined plane have been found to be particularly advantageous. The lowering of the specimen slide occurs as a result of its inherent weight, so that attention must be paid to slow, controlled lowering. The lowering process takes about two seconds.

Another preferred embodiment of the device is characterized in that the support system is provided with two support points or support surfaces for the specimen slide during the raising and lowering. The two support points or support surfaces of the support system ensure a defined support of the specimen slide during the raising and lowering.

Another preferred embodiment of the device is characterized in that the two support points or support surfaces of the support system are disposed at a distance from one another that is smaller than the length of the side of the specimen slide resting on them during the raising and lowering. In this manner, it is ensured that the specimen slide will rest reliably on the support system during the raising and lowering.

Another preferred embodiment of the device is characterized in that the raising and lowering system comprises at least one and particularly two strikers on which the specimen slide rests during the raising and lowering and which can be moved essentially vertically relative to the specimen slide. On the free ends of the striker oriented toward the specimen slide there can be present a support point or support surface for the specimen slide during the raising and lowering.

Another preferred embodiment of the device is characterized in that in the lowered position of the specimen slide the platform is disposed essentially parallel to said slide. The size of the platform is fitted to the size of the surface to be wetted or of the interspace between the platform surface and the specimen slide to be filled with the liquid. The sizes for biochip applications are in most cases standardized, whereas no standardized guidelines exist for the staining of tissues. To minimize liquid consumption, during staining the surface of the platform therefore can be smaller than for the use of biochips. The platform can be made of various materials, for example of stainless steel, aluminum or plastic. The platform can also consist of a film stretched over a frame.

Another preferred embodiment of the device is characterized in that the platform is provided with three support points for the specimen slide in the lowered position. The three support points ensure a stable, statically brought-about support for the specimen slide in the lowered position. The support points are in the shape of elevations of the platform surface and thus form spacing means that ensure a parallel disposition of the platform surface and the underside of the specimen slide in the lowered position.

Another preferred embodiment of the device is characterized in that two of the three support points for the specimen slide in the lowered position are disposed in the region of the side of the specimen slide which during the raising and lowering rests on the support system. This side of the specimen slide is not raised but forms the swiveling axis during the raising and lowering and the specimen slide. The two support points are disposed within the platform.

Another preferred embodiment of the device is characterized in that one of the three support points for the specimen slide in the lowered position is disposed in the region of the side of the specimen slide which during the raising and lowering of the specimen slide rests on the system for raising and lowering the same. In the lowered position of the specimen slide, this support point is disposed above the system for raising and lowering the specimen slide. The other two support points for the specimen slide in the lowered position are disposed above the support system or at the same height as the support system. This ensures that in the lowered position the specimen slide will rest only on the three support points of the platform.

Another preferred embodiment of the device is characterized in that the platform surface is laterally limited by two parallel tracks. The tracks can form the support surfaces for the specimen slide. The tracks, however, can also have a smaller height that the support points of the platform surface. The tracks limit the interspace between the platform surface and the underside of the specimen slide toward the surroundings. In this manner, vaporization of the liquid under the specimen slide is at least reduced.

Another preferred embodiment of the device is characterized in that the end of the platform disposed in the region of the support system is tapered to a point and/or rounded. During the raising and lowering of the specimen slide, this configuration of the end of the platform makes it possible for the liquid to run off or be completely removed from the interspace between the platform surface and the underside of the specimen slide.

Another preferred embodiment of the device is characterized in that the end of the platform disposed in the region of the support system is provided with at least one drain or suction hole. Through this hole, the liquid can be aspirated when needed. The hole preferably has a diameter of 0.5 to 3 mm. The hole can be used not only to remove, but also to supply the liquid. The supplying and removal of the liquid is preferably carried out in the raised position of the specimen slide. The hole can also be disposed outside the platform, namely somewhat below the platform.

Another preferred embodiment of the device is characterized in that the drain or suction hole is disposed in the region of the support system at the end of the platform that is tapered to a point and/or rounded. When the specimen slide is raised, the liquid present in the interspace between the platform surface and the underside of the specimen slide accumulates at the end of the platform that is tapered to a point and/or rounded. The hole disposed there ensures that the liquid can be removed completely.

Another preferred embodiment of the device is characterized in that the end of the platform disposed in the region of the system for raising and lowering the specimen slide is tapered to a point and/or rounded. As a result of this configuration, during the raising and lowering of the specimen slide, the liquid pulls back uniformly from this end toward the opposite end of the platform as a result of adhesion forces.

Another preferred embodiment of the device is characterized in that at the end of the platform facing the support system there is provided a pipetting surface which is partly covered by a part of the underside of the specimen slide. As a result, one end or one side of the specimen slide extends at least slightly beyond the platform. When liquid is applied dropwise to the pipetting surface, it comes in contact with the underside of the specimen slide located above it and, as a result of adhesion forces, is pulled into the interspace between the underside of the specimen slide and the platform surface when the specimen slide is swiveled out of its raised position into its lowered position.

Another preferred embodiment of the device is characterized in that the pipetting surface is disposed below the platform surface. In this manner, a receiving space for the liquid is created between the pipetting surface and a part of the underside of the specimen slide.

Another preferred embodiment of the device is characterized in that the pipetting surface is disposed 0.3 to 0.5 mm below the platform surface. This distance between the pipetting surface and the platform surface was found to be particularly advantageous within the framework of the studies performed.

Another preferred embodiment of the device is characterized in that a step is formed between the platform and the pipetting surface. This step or edge prevents the liquid from flowing back from the interspace between the platform surface and the underside of the specimen slide over the platform end all the way to the end of the specimen slide on this side. This ensures that the liquid will be removed completely through the suction hole or drain disposed at this platform end.

Another preferred embodiment of the device is characterized in that the pipetting surface is inclined toward the platform. The slope of the platform ensures that the liquid can reach the interspace between the platform surface and the underside of the specimen slide.

Another preferred embodiment of the device is characterized in that at least one hole for supplying and/or removing the liquid is provided in the pipetting surface. This ensures that the liquid can be measured and supplied automatically to the pipetting surface through a suitable channel system or hose system.

Another preferred embodiment of the device is characterized in that the platform can be swiveled relative to the system for carrying the specimen slide. The raising and lowering of the platform relative to the specimen slide can thereby be accomplished in a simple manner.

Another preferred embodiment of the device is characterized in that on the system for carrying the specimen slide there is provided a hinge allowing the platform to swivel between the raised and the lowered position. The hinge can comprise, for example, two pins connected with the platform and each of which being rotatably lodged in a bearing eye provided on the specimen slide-carrying system.

Another preferred embodiment of the device is characterized in that on the platform there is provided a swivel arm whereby the platform can be swiveled between the raised and the lowered position. The swivel arm makes possible an automatic raising and lowering of the platform relative to the specimen slide.

Another preferred embodiment of the device is characterized in that the platform is disposed above the specimen slide-carrying system. In this embodiment, the object to be examined is disposed on the top side of the specimen slide. The liquid for wetting the object that is to be examined is introduced into the interspace between the underside of the platform and the top side of the specimen slide.

Another preferred embodiment of the device is characterized in that in the marginal region of the platform there is provided a pipetting channel through which the liquid can be applied onto the specimen slide and removed from the specimen slide. The liquid is applied to and removed from the specimen slide in the raised position of the platform. When the platform is lowered relative to the specimen slide, the liquid distributes itself uniformly in the interspace between the underside of the platform and the top side of the specimen slide.

A preferred embodiment of the device is characterized in that the specimen slide-carrying system comprises two tracks on which the edges on the long side of the specimen slide can come to rest. The tracks ensure a reliable and stable support for the specimen slide on the specimen slide-carrying system.

The afore-mentioned objective is reached by use of a method for wetting, particularly for staining or hybridizing, biological materials such as tissues, DNA, RNA, biochips etc, with a liquid, the specimen slide being moved, particularly swiveled, relative to the platform so as to uniformly distribute or remove the liquid between the specimen slide and the platform. In the lowered position of the specimen slide, the underside of the specimen slide is disposed parallel to the platform surface. Alternatively, at the end opposite to the suction hole, the specimen slide can be lowered as far as the platform provided the anterior support point is not omitted. In this manner, a negative angle is created as a result of which the liquid volume is further reduced. When the specimen slide is swiveled about one of its sides or corners, adhesion forces return the liquid to the tapered end of the gap between the platform and the underside of the specimen slide. In the raised position of the specimen slide, the liquid can be supplied to the tapered end of the gap. When the specimen slide is lowered, the liquid distributes itself, starting from the pointed end of the gap, over the entire interspace between the platform surface and the underside of the specimen slide. In the lowered position of the specimen slide, the interspace is completely filled. When the specimen slide is again raised, namely swiveled about the same side as during the lowering, the liquid again pulls back from the interspace to the pointed end of the conical gap. The swiveling rate must be controlled during both the raising and the lowering of the specimen slide. At the beginning of the raising, the swiveling rate is somewhat reduced and amounts to about two seconds for 5 mm. This prevents the tearing of the liquid film between the platform surface and the underside of the specimen slide. By repeatedly raising and lowering the specimen slide, different liquids can be mixed in the interspace between the underside of the specimen slide and the platform surface. During the cleaning of the underside of the specimen slide and of the platform surface, it has been found advantageous repeatedly to raise and lower the specimen slide while introducing a cleaning liquid into the interspace.

A preferred embodiment of the method is characterized in that, during the raising and lowering, the specimen slide is swiveled through 1 to 25° and particularly through 8 to10°. In the course of studies concerning the present invention, these swiveling angles were found to be particularly advantageous.

Other advantages, features and details of the invention will be set forth in the following descriptions of the various embodiments and by reference to the drawings, in which:

FIG. 17 is a top view of another embodiment of the device of the invention;

FIG. 18 is a sectional view along line XVIII-XVIII in FIG. 17;

FIG. 19 is an oblique frontal perspective view of the upper part represented in FIGS. 17 and 18;

FIG. 20 is a lateral view of another embodiment of the device of the invention;

FIG. 21 is a sectional view along line XXI-XXI in FIG. 22 of the device shown in FIG. 20;

FIG. 22 is a top view of the device of FIG. 20, and

FIG. 23 is a perspective representation of the device of FIG. 20.

Figure 1:
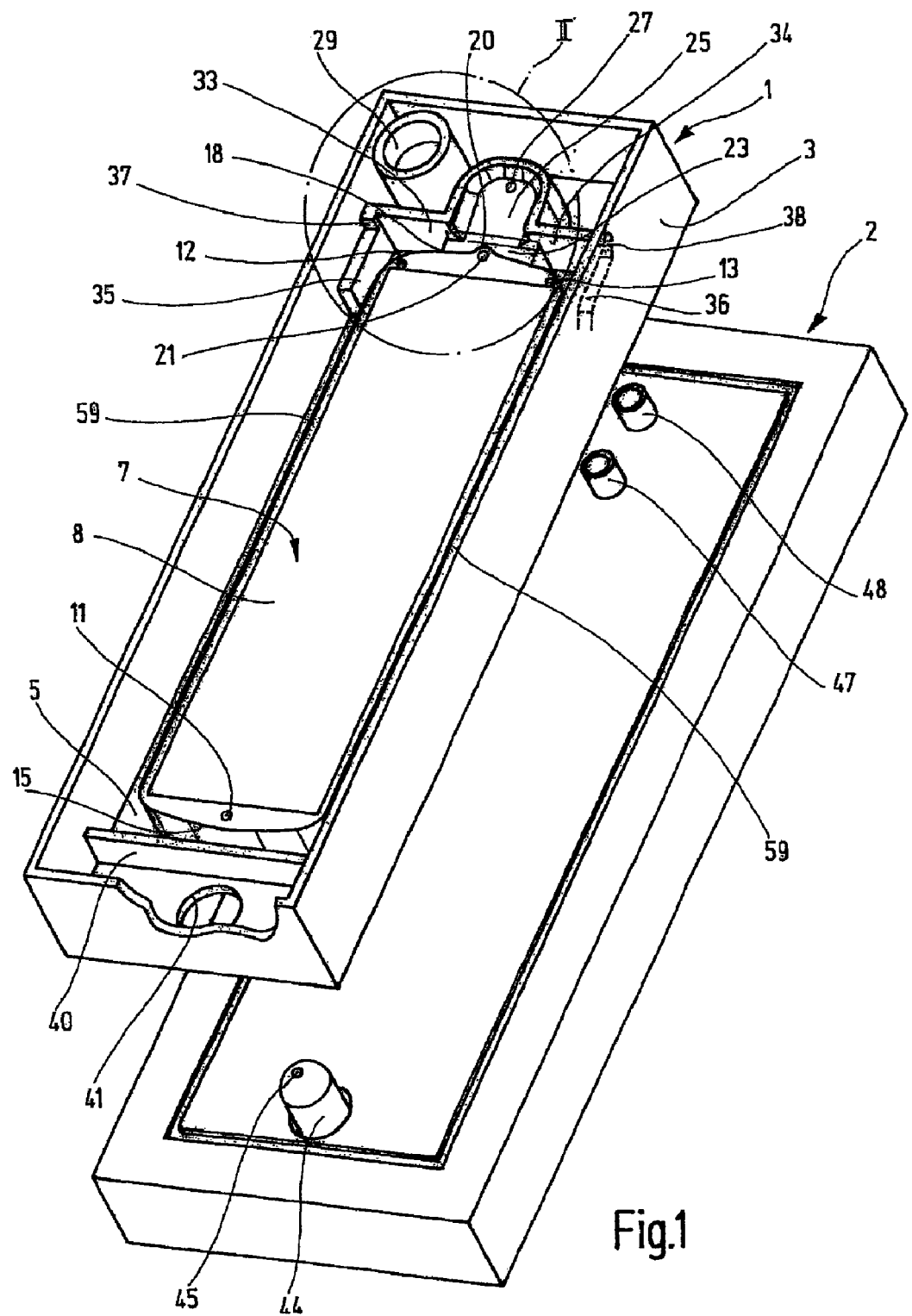
FIG. 1 shows an exploded view of an embodiment of the device of the invention with a system for raising and lowering a specimen slide on one of its short sides.

The exploded view in perspective of the device in FIG. 1 shows an upper part 1 and a lower part 2 of a device for wetting objects that are disposed on the bottom side of specimen slides. Upper part 1 is formed by a rectangular frame 3 with a bottom 5. Part 1 is also provided with a platform 7 which has a rectangular reaction surface 8.

On the surface of platform 7 are present three elevated support points 11, 12 and 13. Support point 11 is disposed on a rounded end 15 of platform 7. The two support points 12 and 13 are disposed on a rounded end 18 of platform 7, said rounded end being located opposite rounded end 15. The rectangular surface 8 extends between the two rounded ends 15 and 18 of platform 7. On one short side of reaction surface

8, about halfway in-between, is located support point 11. On the opposite short side of reaction surface 8 are located the two support points 12 and 13, each at the end of the corresponding side.

At the rounded end 18 of platform 7 there is formed an essentially semicircular projection 20 that fits into suction hole 21 which extends at an angle through platform 7. The purpose of suction hole 21 is to draw off the liquid from reaction surface 8.

At rounded end 18, on platform 7, there is provided a step 23 which becomes a pipetting surface 25. Pipetting surface 25 is provided with an essentially rectangular base surface the ends of which that face away from step 23 are rounded. Moreover, pipetting surface 25 is tilted toward platform 7. A supply opening 27 for the liquid is provided at the upper end of pipetting surface 25.

On the left side of pipetting surface 25, as seen from the top, in one corner of frame 3 there is provided for the liquid a reservoir 29 in the form of an essentially round cylindrical jacket. Reservoir 29 is intended to receive the liquid in liquid-tight fashion and in the transport condition is closed, for example, by a film. Before use, the film can be removed, and the liquid contained in reservoir 29 applied dropwise onto pipetting surface 25 with the aid of a pipette.

Figure 2:
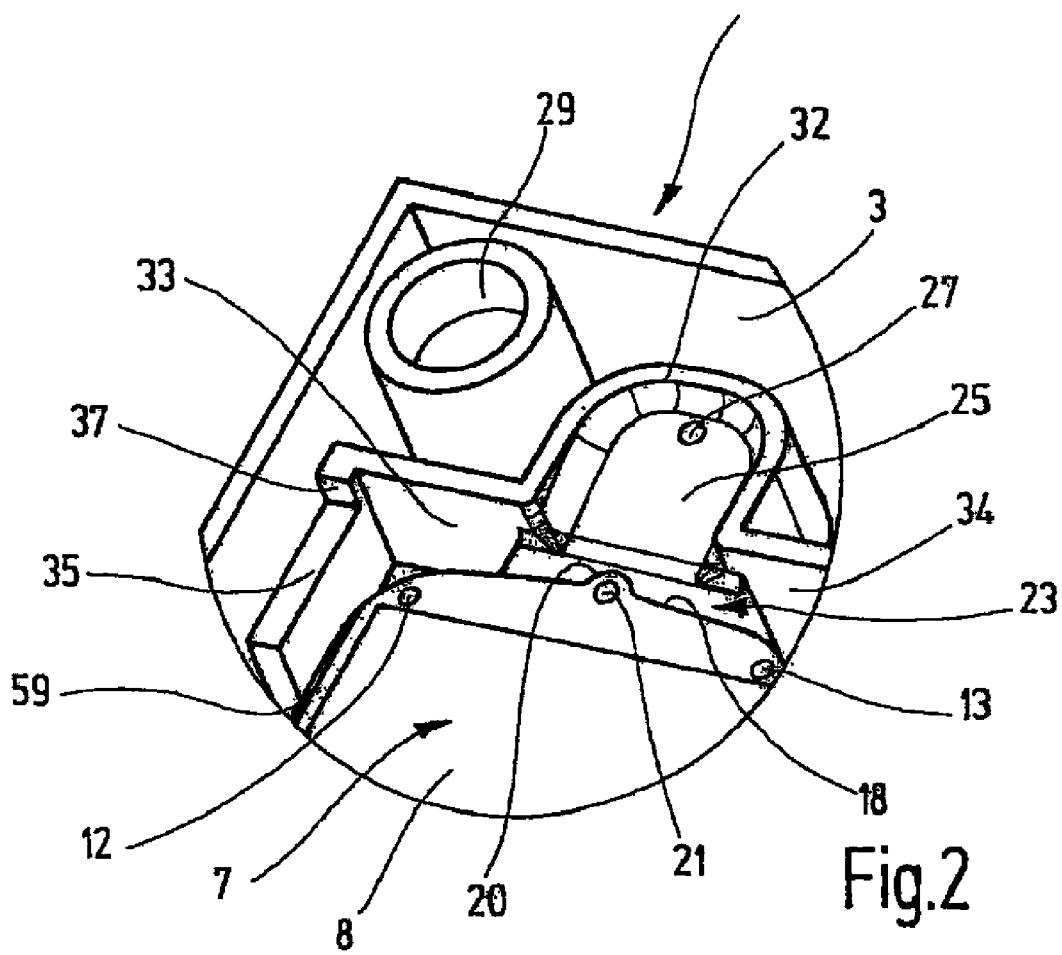
FIG. 2 shows an enlarged cut-out from FIG. 1 which in FIG. 1 is indicated by II.

From the enlarged cut-out presented in FIG. 2, it is quite evident that pipetting surface 25 is limited by an enclosing wall 32 which, as seen from the top, is essentially U-shaped. From the ends of enclosing wall 32 extend straight connecting walls 33 and 34 which are disposed parallel to the short sides of the rectangular reaction surface 8. The free ends of connecting walls 33 and 34 are bent in rectangular manner and run parallel to the long sides of rectangular reaction surface 8. The bent ends of connecting walls 33 and 34 form support surfaces 35 and 36 for a specimen slide during raising and lowering. Support surfaces 35 and 36 are at the most as high as support points 12 and 13. Moreover, at the bent ends of connecting walls 33 and 34 there are formed stopping surfaces 37 and 38 for a specimen slide during raising and lowering said surfaces preventing an undesirable displacement of the specimen slide during raising and lowering.

It can be seen from FIG. 1 that at the rounded end 15 of platform 7 there is present a bar 40 for the reinforcement of frame 3. On the side of bar 40 facing away from platform 7, which bar is disposed at an angle to frame 3, a through-hole 41 is hollowed out in bottom 5. Through-hole 41 makes it possible for a striker 44 to pass through, said striker being able to be driven and actuated to move back and forth in the lower part 2. At the free end of striker 44 there is provided a punctiform support surface 45 for one end of a specimen slide (not shown). The purpose of striker 44 is to raise a specimen slide resting on support points 11 to 13 of platform 7.

On the end of lower part 2 opposite striker 44 are present two coupling parts 47 and 48. Coupling part 47 is intended to provide a liquid-tight connection with suction hole 21 that is located at the rounded end 18 of platform 7. The purpose of coupling end 48 is to provide a liquid-tight connection with supply opening 27 formed in pipetting surface 25.

Figure 3:
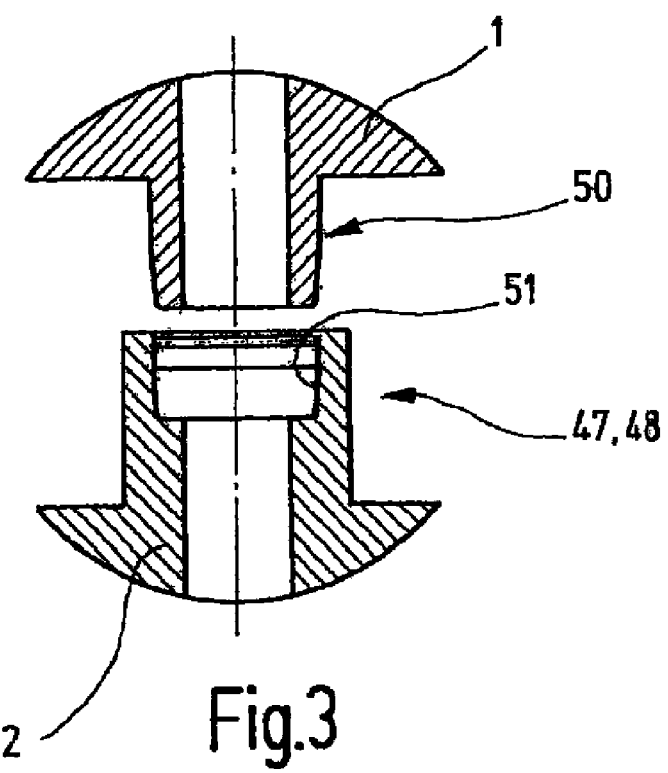
FIG. 3 is a sectional view of a detail of FIG. 1.

FIG. 3 is an enlarged cross-sectional view of the manner in which coupling parts 47 and 48 provided on lower part 2 are coupled with upper part 3. In upper part 1 is always provided an insertion part 50 which can enter a complementary opening 51 of coupling parts 47, 48. Both the insertion part 50 and opening 51 are slightly conical in shape to ensure a liquid-tight connection between the two parts in the assembled condition.

Figure 4:
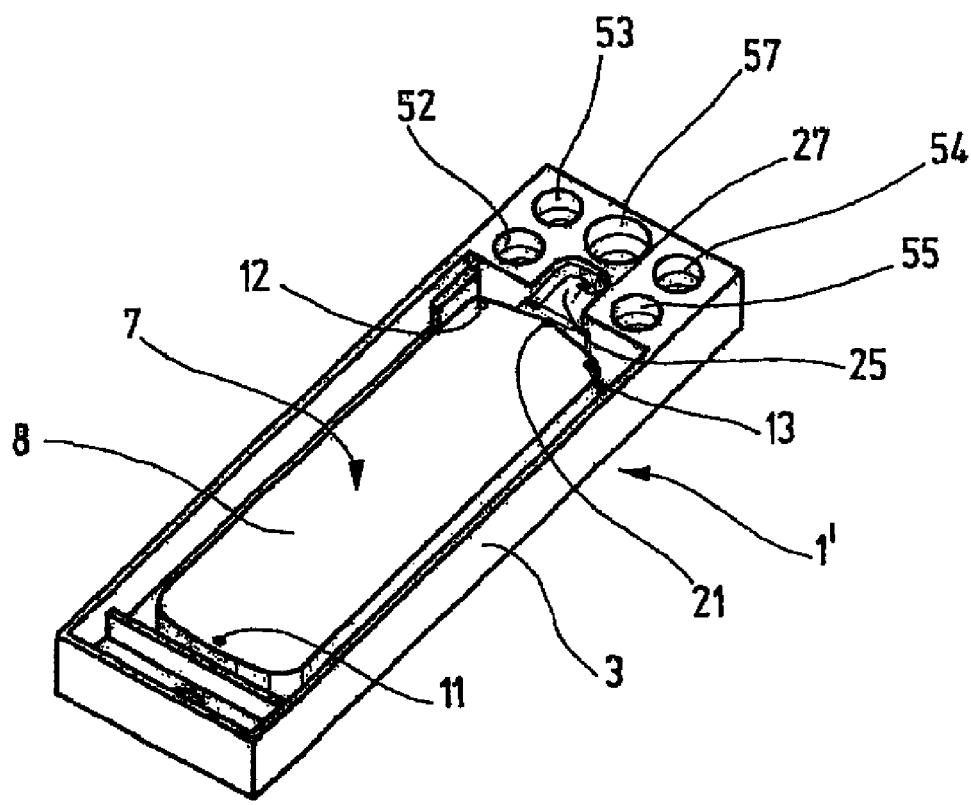
FIG. 4 is an oblique perspective view from above of a variant of the upper part of the embodiment shown in FIG. 1.
Figure 5:
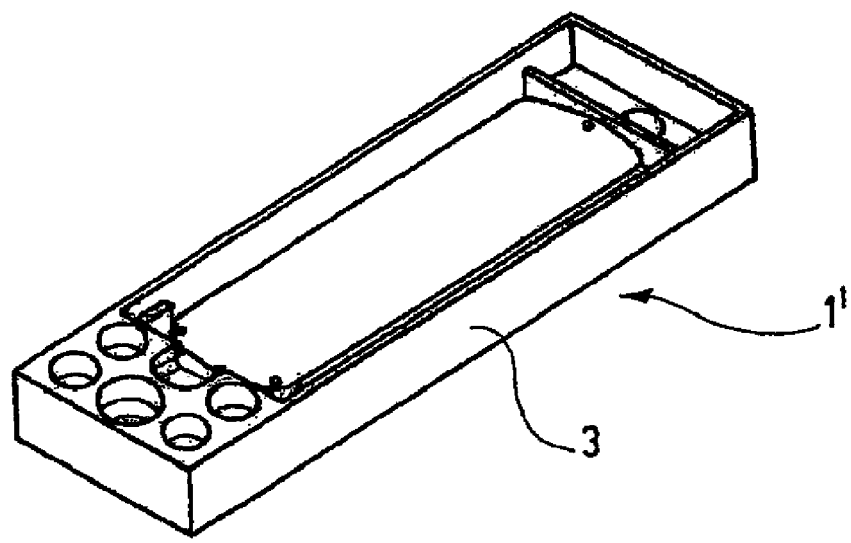
FIG. 5 shows the upper part represented in FIG. 4 in the inverted position.

FIGS. 4 and 5 are views in perspective of an upper part 1' which resembles the upper part 1 of the device shown in FIG. 1. Equal parts are indicated by equal reference numerals so that in this respect the reader may refer to the description of FIG. 1.

In upper part 1' represented in FIGS. 4 and 5, not only one reservoir, but several reservoirs 52, 53, 54 and 55 for different liquids are provided in the vicinity of pipetting surface 25. Reservoirs 52 and 55 are disposed laterally next to pipetting surface 25. On the side of pipetting surface 25 facing away from platform 7 is located a mixing cup 57 wherein different liquids can be mixed with one another before they are applied to pipetting surface 25. Reservoirs 53 and 54 are disposed to the side of mixing cup 57. In the reservoirs are stored prepared, measured amounts of, for example, labeled ISH [in-situ hybridization] probes or antibodies that are removed by the pipetting robot only when needed for actual use.

Figure 6:
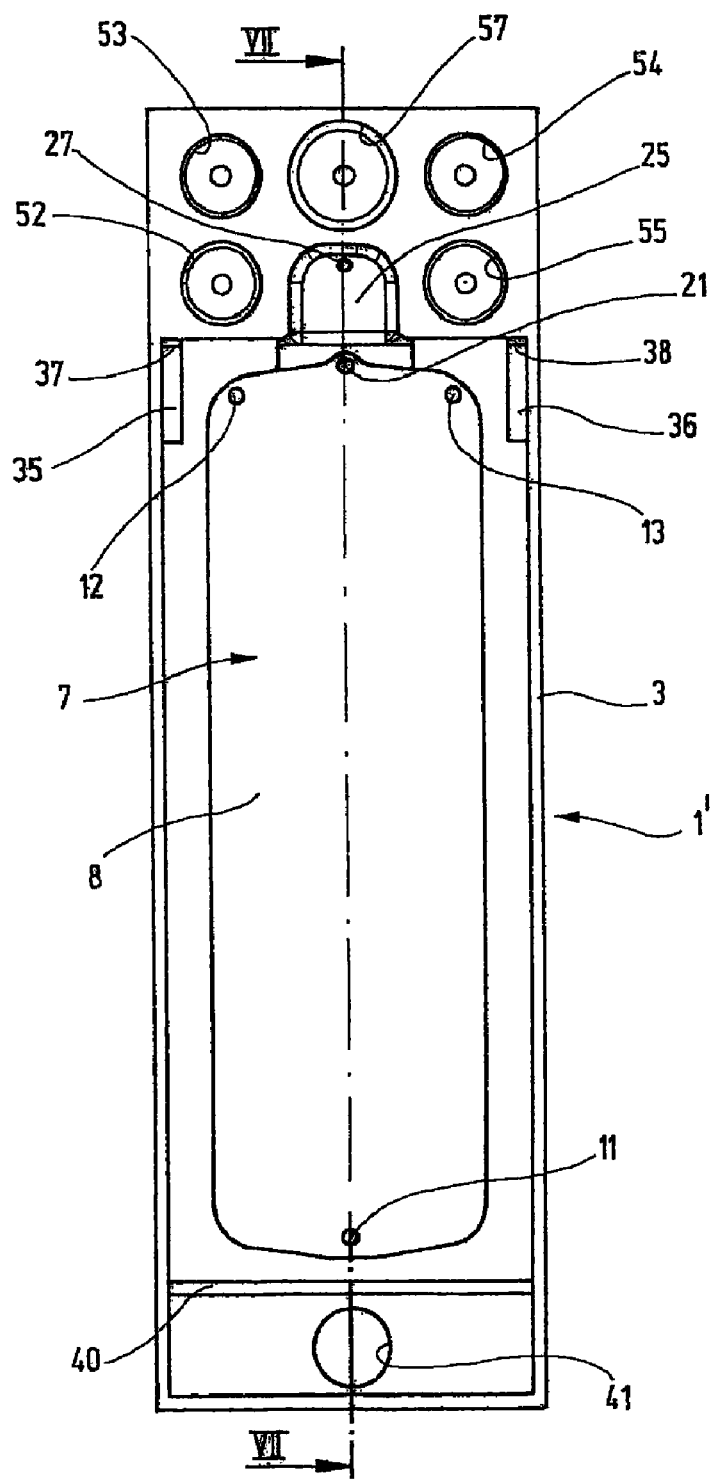
FIG. 6 is a top view of the upper part represented in FIG. 4.
Figure 7:
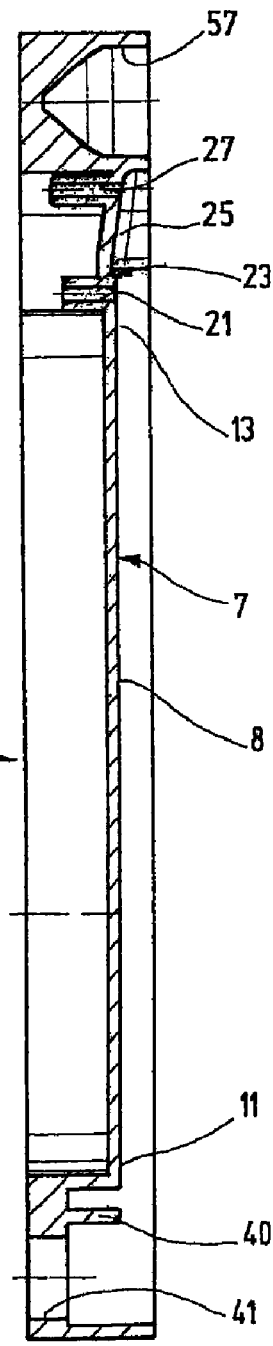
FIG. 7 is a cross-sectional view along line VII-VII in FIG. 6.

It can be seen from FIGS. 6 and 7 that upper part 1', represented in top view and in cross-section, just like upper part 1 represented in FIG. 1 consists of a single piece. Upper part 1,1' is preferably made of plastic by injection molding. Platform 7 can have a convex underside to ensure uniform heat transfer from a hot plate to the platform when the convex underside of the platform is pressed against the hot plate.

Platform 7 can consist of surfaces of different sizes, the sizes being defined depending on the application. For example, internationally standardized sizes are specified for biochip applications whereas for staining tissues there are no standardized guidelines. To keep the consumption of reagents as low as possible, for tissue studies the platform surface can therefore be smaller than for the use with biochips.

For the embodiments represented in FIGS. 1 to 7, reaction surface 8 is somewhat smaller than a specimen slide. In the lowered position, the specimen slide (not shown) rests on support points 11 to 13 that protrude from the surface of platform 7. In both the raised and the lowered position, the specimen slide rests with one short side on stop surfaces 37 and 38, the specimen slide protruding slightly beyond the corresponding platform end. The opposite end of the specimen slide protrudes further beyond the corresponding end of platform 7. In the lowered position, the further protruding end of the specimen slide is disposed above striker 41. When the specimen slide is not in the raised position, support points 11 to 13 bear the specimen slide.

When striker 44 (see FIG. 1) is moved out of lower part 2, the punctiform support surface 45 of striker 44 touches the underside of the specimen slide. Further movement of striker 44 at first raises the specimen slide from support point 11 at one end of platform 7. When striker 44 is moved even further out of lower part 2, the specimen slide lifts from support points 12 and 133 as well and comes to rest on support surfaces 35 and 36 which at the most are as high as support points 12 and 13. In the raised position of the specimen slide, the liquid present on the platform can pull back as far as suction hole 21 and can thus be completely removed by suction.

Support points 11 to 13 for the specimen slide on platform 7 serve to keep the reaction surface 8 parallel to the underside of the specimen slide. When the gap of the interspace between the platform surface and the underside of the specimen slide is filled with one or more liquids, the desired biochemical and chemical reactions can take place.

Suction hole 21 can also be used as a supply hole. Moreover, to the left or right of suction hole 21 there can be provided one or more holes performing the functions of "filling" or "draining". For tissue staining, it is particularly advantageous if in addition to suction opening 21 there is provided another hole in platform 7 through which dewaxing solutions can be supplied or removed. Separate removal of dewaxing solutions is of particular advantage because normally the paraffin present in the dewaxing liquid after dewaxing will plug up the suction hoses. Suction hole 21 could also be plugged by the dewaxing liquid which would prevent further treatment of the tissue section.

It can be seen from FIG. 7 that pipetting surface 25 is inclined toward platform 7. A part of pipetting surface 25 is disposed slightly below reaction surface 8. Pipetting surface 25 is intended to receive the liquid in the form of drops which, when they come in contact with the overlying underside of the specimen slide, are completely pulled by capillary forces over step 23 into the gap between the surface of platform 7 and the underside of the specimen slide. Pipetting surface 25 is disposed at one end of platform 7 and preferably lies 0.3 to 0.5 mm lower than platform 7. Pipetting surface 25 can also be disposed parallel to the surface of platform 7.

It is shown in FIGS. 1 and 2 that platform 7 can also be provided with a track 59 on each side. The tracks can serve as alternatives to support points 11 to 13. In addition, the tracks act as a barrier against the escape of liquids that can vaporize when heated. The tracks can also be provided in addition to support points 11 to 13 and be lower than these.

For an automatic use of the device, which is also referred to as hybridization chamber, the heating/cooling and liquid handling functions must be ensured. For this reason, an arresting mechanism is provided between upper part 1 and lower part 2, said mechanism making it possible to press the underside of the platform onto lower part 2 while at the same time keeping coupling parts 47, 48 and 50 connected to each other. A drive and a control mechanism for the movement of strikers 44 are integrated into lower part 2. The arresting action between upper part 1 and lower part 2 can be brought about by the contact pressure of the side walls, a clamp/holding construction, a clamp-grid holding device or a sliding mechanism at the side walls.

Figure 8:
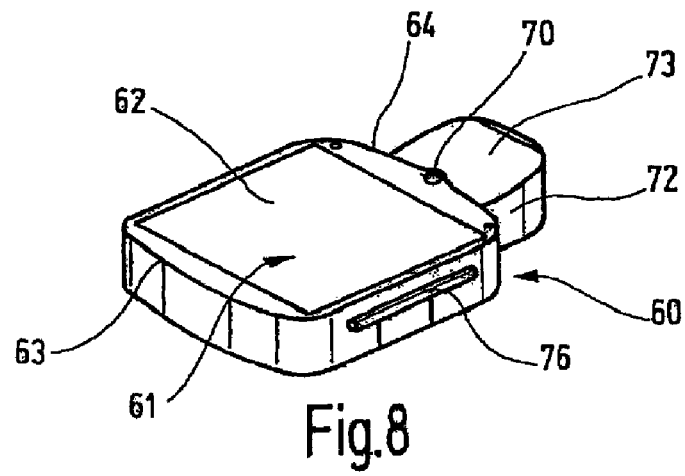
FIG. 8 is an oblique frontal perspective view of the upper part of a second embodiment of the device of the invention.
Figure 9:
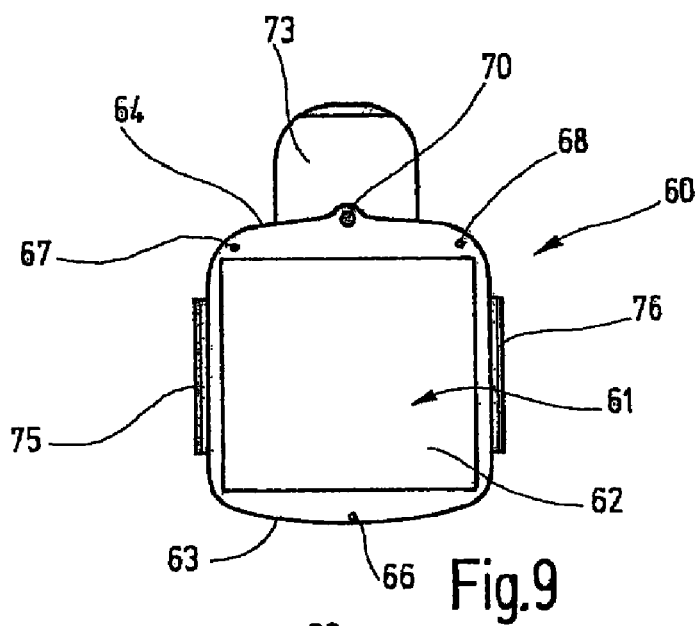
FIG. 9 is a top view of the upper part represented in FIG. 8.

FIGS. 8 and 9 show an upper part 60 according to a further embodiment of the invention. On upper part 60 there is provided a platform 61 with a reaction surface 62. Platform 61 has two rounded ends 63 and 64. On platform 61 are provided three support points 66, 67 and 68 for a specimen slide in the lowered position. Moreover, a suction hole 70 for the liquid is provided at rounded end 64.

Upper part 60 has an attachment 72 with a pipetting surface 73. Pipetting surface 73 is inclined toward platform 61 and, at least partly, disposed beneath reaction surface 62.

On the sides of and protruding from upper part 60 are provided two gripping strips 75 and 76. Upper part 60 is made as a single piece from a plastic material, for example by injection molding.

Figure 10:
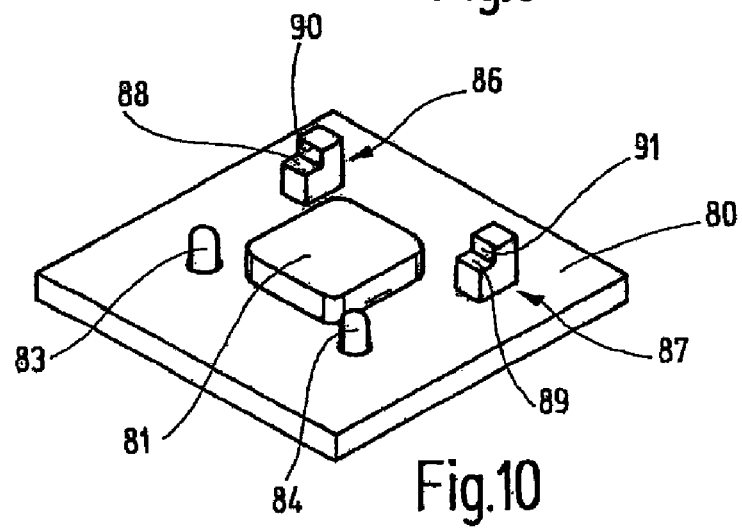
FIG. 10 is an oblique frontal perspective view of the lower part corresponding to the upper part represented in FIGS. 8 and 9.

FIG. 10 shows a view in perspective of lower part 80 corresponding to upper part 60 represented in FIGS. 8 and 9. Lower part 80 is shaped as a square plate on the center of which is disposed a heating plate 81. Besides heating plate 81, two strikers 83 and 84 are provided in lower part 80, said strikers being movable back and forth. Strikers 83 and 84 are disposed on one side and at the corners of heating plate 81. On the opposite side of heating plate 81 are provided two supports 86 and 87 for the specimen slide during raising and lowering. On supports 86 and 97, there are provided horizontally disposed support surfaces 88 and 89 for a specimen slide during raising and lowering. Moreover, on supports 86 and 87 are provided vertically disposed stop surfaces 90 and 91 for the specimen slide.

Figure 11:
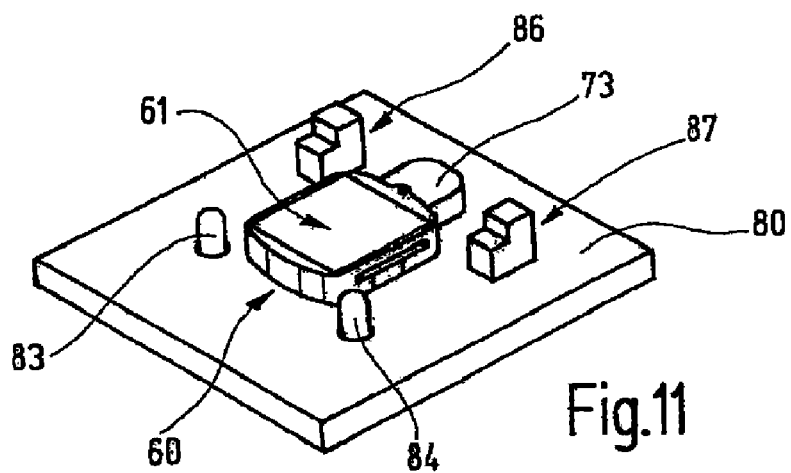
FIG. 11 is an oblique frontal perspective view of the upper part represented in FIGS. 8 and 9 when assembled with the lower part represented in FIG. 10.

FIG. 11 shows upper part 60 and lower part 80 in the assembled condition. Upper part 60 is disposed so that platform 61 is located above the heating plate. Upper part 60 is fastened to lower part 80, for example by means of a snap-on connection.

Figure 12:
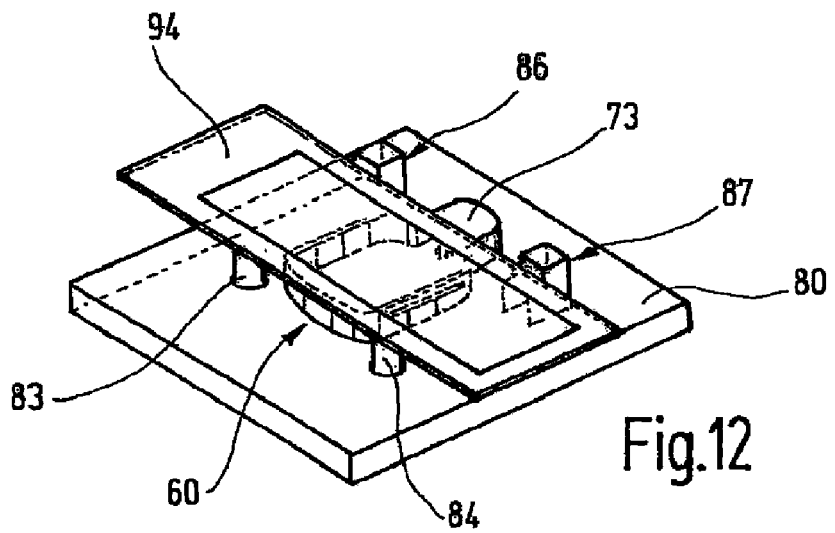
FIG. 12 shows the device of FIG. 11 with a specimen slide resting on top.

FIG. 12 shows a specimen slide 94 resting on the device represented in FIG. 11. In the lowered position, specimen slide 94 rests only on support points 66 to 68 of platform 61. When strikers 83 and 84 raise the specimen slide, said slide lifts off the support points 66 to 68 and comes to rest on the support surfaces 88 and 89 provided on supports 86 and 87.

The device represented in FIG. 12 differs from the embodiments represented in FIGS. 1 to 7 in that only a relatively small segment of specimen slide 94 rests on platform 61. As a result, the volume of liquid needed for the examination can once again be markedly reduced, for example to a volume of 25 to 50 μL. With decreasing platform size, however, the distance between the support points on the platform is also reduced. As a result, the positioning of the specimen slide on the platform itself can become unstable.

Figure 13:
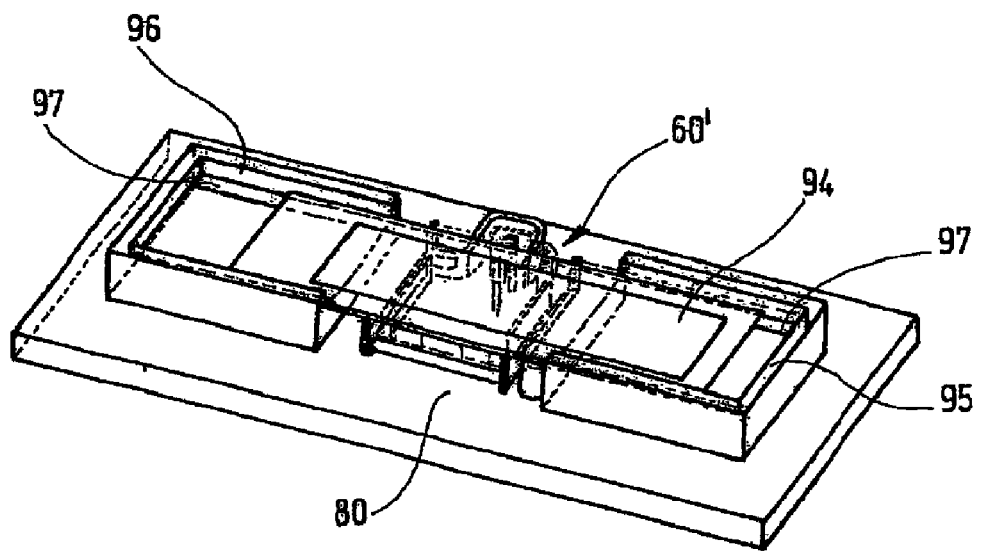
FIG. 13 is an oblique frontal perspective view of another embodiment of the device of the invention.

FIG. 13 shows another embodiment with an upper part 60' similar to that represented in FIG. 12. Upper part 60' is disposed on a rectangular lower part 80'. Lower part 80' is rectangular and both longer and wider that specimen slide 94. On lower part 80' there are disposed two U-shaped carrier elements 95 and 96 each with two branches. On the two branches of the U-shaped carrier elements 95 and 96 there are provided support tracks 97 constituting support surfaces for the ends of specimen slide 94. The two U-shaped carrier elements 95 and 96 are disposed on both sides of upper part 60' and thus at a distance from one another such that specimen slide 94 can be displaced in the longitudinal direction. The displaceability of specimen slide 94 on carrier elements 95 and 96 ensures that different segments of specimen slide 94 can be disposed above upper part 60'. Specimen slide 94 can thus be displaced on the platform of upper part 60'.

Figure 14:
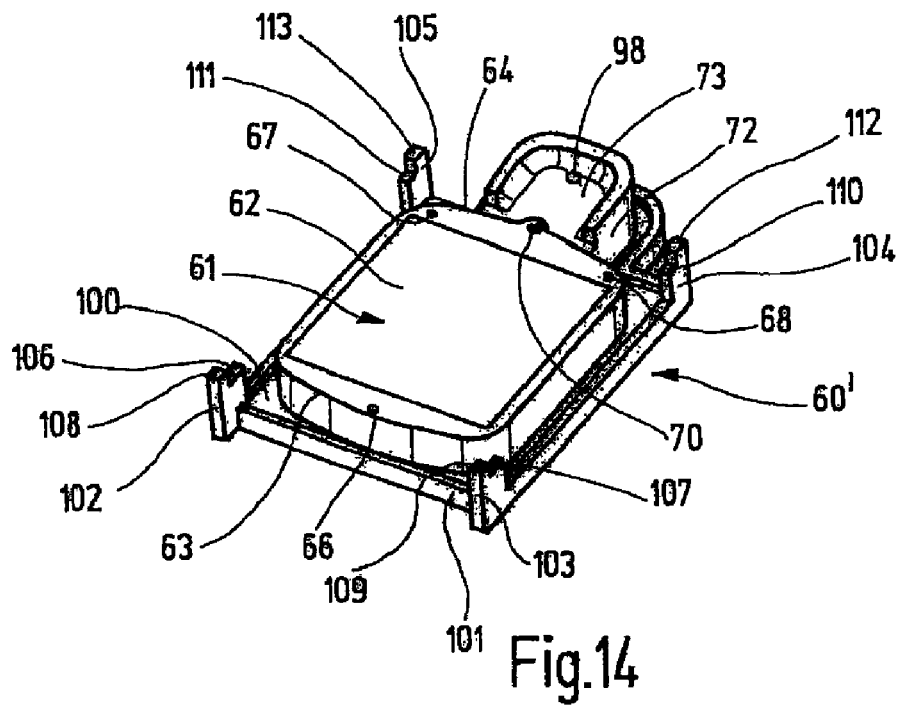
FIG. 14 is an oblique frontal perspective view of the upper part of the device represented in FIG. 13 by itself.
Figure 15:
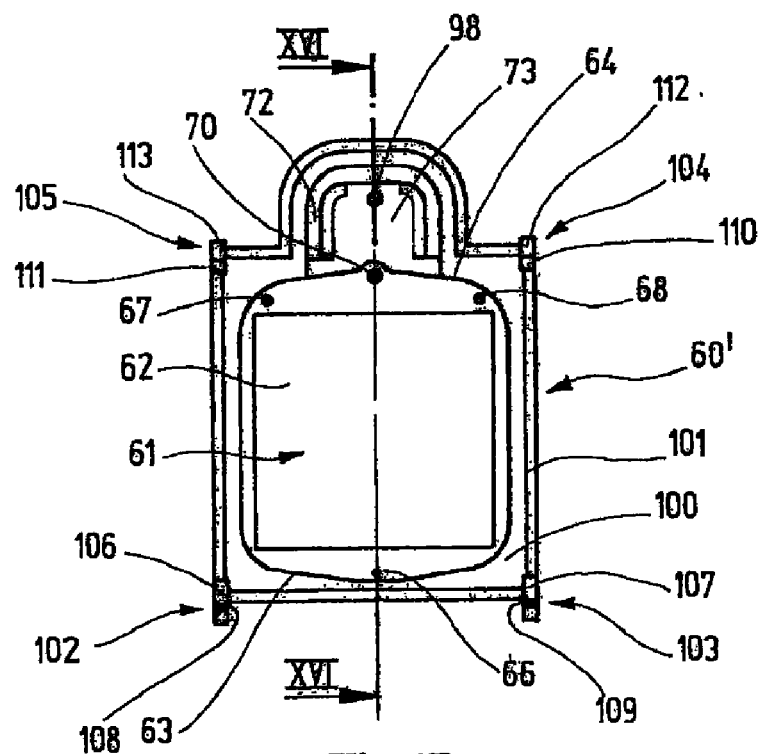
FIG. 15 is a top view of the upper part of FIG. 14.
Figure 16:
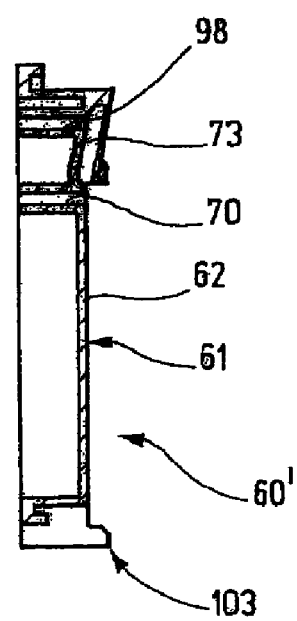
FIG. 16 is a sectional view along line XVI-XVI in FIG. 15.

FIGS. 14 to 16 show different views of upper part 60'. For simplification, because upper part 60' resembles upper part 60 represented in FIGS. 8 and 9, identical parts are indicated by the same reference numerals. For the identical parts of the two embodiments, the reader is referred to the description of FIGS. 8 and 9. In the upper part 60' represented in FIGS. 14 to 16, pipetting surface 73 is provided with a supply opening 98 for a liquid. Supply opening 98 is disposed in the upper region of pipetting surface 73 to ensure that the liquid introduced will flow downward on pipetting surface 73 which is inclined toward platform 61.

In upper part 60' represented in FIGS. 14 to 16, platform 61 and attachment 72 are connected with a frame 101 via a bottom 100. The frame is rectangular and in the region of attachment 73 adapted to the shape of said attachment. At the corners of frame 101 there are provided supports 102, 103, 104 and 105. Supports 102 and 103 are fitted with support surfaces 106 and 107 which, however, are not used in normal operation, because in the lowered position, on this side of upper part 60', the specimen slide rests on support point 66 of platform 61. When the specimen slide is raised, said slide moves away from support surfaces 106 and 107 so that the specimen slide even when raised does not rest on support surfaces 106 and 107. Moreover, supports 102 and 103 are fitted with stop surfaces 108 and 109 for the specimen slide.

Supports 104 and 105 are provided with support surfaces 110 and 111 on which the specimen slide rests during the raising. Moreover, on supports 104 and 105 there are provided stop surfaces 112 and 113 for the specimen slide which together with stop surfaces 108 and 109 prevent crosswise displacement of said slide.

FIGS. 17 to 19 show different views of the upper part of another embodiment of the device of the invention. The upper part has a platform 170 above which a specimen slide can be disposed. The interspace between platform 170 and the underside of the specimen slide (not shown) can be supplied with a liquid by means of a pipetting surface 175. The liquid can be applied to pipetting surface 175 either with the aid of a pipette or through a supply opening 177 provided in pipetting surface 175. Pipetting surface 175 is inclined toward platform 170, the end of pipetting surface 175 that faces platform 170 being disposed slightly below the platform surface. Between pipetting surface 175 and platform 170 is a groove 179 in the center of which is provided an opening 180 for the removal of the liquid. Removal opening 180 has a diameter of about 1 mm. The advantage of the disposition and of the shape of removal opening 180 is that the liquid to be removed can be removed without the use of an additional pump.

FIGS. 20 to 23 show different views of a device of the invention in which the platform can be swiveled relative to the specimen slide. A device 201 serves to carry a specimen slide 203. For this purpose, the carrier device 201 has a supporting frame 205 that is provided with three tracks 207, 208 and 209. Tracks 207 and 209 form the long sides of a rectangle and are connected by track 208. Tracks 207 to 209 form the support surfaces for specimen slide 203.

Approximately in the middle of the long sides of supporting frame 205 are located essentially triangular attachments 211, 212 which are provided with recesses for the rotatable bearing of bearing pins 215, 216. Bearing pins 215, 216 are attached to a platform 220 which is surrounded by a platform frame 222. Above the platform frame, platform 220 is connected with a swivel arm 224 by which platform 220 can be swiveled about the long axis of bearing pins 216, 216 relative to device 201 for carrying specimen slide 203.

At the ends of tracks 207, 209 facing away from track 208 are located two stops 228, 227 for specimen slide 203. Stops 227, 228 are in the form of elevations intended to prevent an undesirable sliding of specimen slide 203 out of device 201. In FIG. 22, specimen slide 203 is shown in a position in which it is not yet completely inserted into device 201.

When the device shown in FIGS. 20 to 23 is operating, an automatically guided pipette removes the required reagent, for example from a reagent strip disposed on the long side of the platform, and transports it to a pipetting channel 230 disposed at the end of plat-form 220 that is tapered to a point. The pipette (not shown) or the pipetting needle dips slightly into pipetting channel 230 and releases the reagent. At the same time, by the downward movement of the pipetting needle during the immersion into pipetting channel 230, swiveling arm 224 of platform 220 is pressed downward, namely toward specimen slide 203, by a pin (not shown) attached to the pipetting arm. As a result, by means of hinge 211, 212, 215, 216 platform 220 tilts upward and is thus placed in a crosswise position. The liquid reagent pipetted in remains between the top side of specimen slide 203 and the lower end of pipetting channel 230 until the pipetting needle is displaced upward and the pin is at the same time displaced from swiveling arm 224 of platform 220. As a result of its inherent weight or by the action of an additional spring system, platform 220 then moves downward. Subsequently, the liquid reagent spreads out between the upper side of specimen slide 203, which is in the down position, and the fastened tissue or some other biological material and the complete underside of platform 220 so that the object to be studied is wetted.

When the liquid reagents are sucked off, the same or another pipetting needle with the pin attached to the swiveling arm is lowered into pipetting channel 230. As the pipetting needle drops, the pin again presses against swiveling arm 24 of platform 220, whereby platform 220 is again tilted via hinge 211, 212, 215, 216. As a result, the liquid reagent pulls back to the side of platform 220 to which pipetting channel 230 is attached. There, the liquid can be sucked off by the introduced pipetting needle.

The device of the invention and the method of the invention are used, for example, for hybridization. To automate the method of the invention with the aid of the device of the invention, it is possible to use standard, commercially available assemblies of structural groups. These are combined and controlled by appropriate software. For automated operation, besides a heating/cooling system, pumps for supplying and removing liquids as well as a pipetting component or pipetting platform with all the required auxiliary equipment are needed. In fully automatic operation, the functions of filling of the reaction/hybridization chambers (in the following referred to as chambers) between the platform surface and the underside of the specimen slide with reagents and auxiliary reagents (in the following referred to as liquids), removing the liquids from the chambers, heating and cooling the liquids in the chambers and removing the liquids from optionally provided reservoirs must be combined with one another by appropriate software control.

The described chambers make it possible to use basically two methods for filling them. The first and preferred method consists of filling through a pipetting system. To this end, by means of a standard pipetting system, the reagent liquid or the auxiliary reagents are taken, for example sucked into the pipette held by a pipetting arm, either from the reservoir of the chamber or from a separate storage container, and applied dropwise onto the pipetting surface of the chamber or of the device. From the pipetting surface, the liquid then, via the step, reaches the platform and penetrates between the underside of the specimen slide and the platform surface. The specimen slide is then lowered from the raised position until it rests on the support points of the platform. In this manner, the liquid distributes itself onto the entire platform surface.

According to a second method, the liquid can be taken from storage containers via a hose system (pipeline system) and guided through hole 70 onto the surface of the platform. The specimen slide is then lowered from the raised position as a result of which the liquid distributes itself onto the entire surface of the platform.

The chamber is emptied in two steps. In the first step, the specimen slide is raised as a result of which the liquid present between the underside of the specimen slide and the platform surface pulls back to the side of the specimen slide that is not raised and collects around the suction hole. In the second step, the liquid is completely removed by suction through suction hole 70 by use of a pump, preferably a peristaltic pump, connected through a hose.

The chambers are constructed so that they may be used for various applications. For some of these applications, particularly for in-situ hybridization or even general hybridization of, for example, microarrays, the chambers must be heated and cooled. This is true particularly for the in-situ polymerase chain reaction [PCR] or for biochips, for which the generally known PCR cycles must be used. This means, for example, that within a few seconds it is necessary to cool from 94° C. to 72°C., and then to reheat to 94° C. Other temperature levels are, for example, 55° C. or 23° C. For applications in the field of immunohistochemistry, the possibility of heating to 45° C. will suffice. If the ambient temperature does not exceed 25° C., active cooling is not necessary. Heating gives the best results in terms of acceleration of the biochemical process. An active increase in temperature could be omitted if one is prepared to wait for the completion of the process over a longer period of time. In general, the use of special stains requires no increase in temperature. For such uses, the provision of a heating/cooling mechanism could therefore be omitted.

Because the chambers or devices of the invention are suitable for all applications, it is preferred from an economical point of view to provide the instrument with a heating/cooling system so that all applications can be carried out in the same laboratory. The preferably used heating/cooling technology comprises the Peltier elements. In this manner, rapid heating and cooling is ensured.

Alternatively, the instrument or the device can be equipped with resistance heating. Active cooling can be brought about with a fan or with the aid of a cooling system of the kind commonly used in refrigerators. Alternatively, the ambient temperature itself can be used for cooling.

A further alternative would be water heating/cooling supplied via a built-in or attached instantaneous water heater. This method is particularly advantageous when instead of being controlled individually, all chambers are heated or cooled in parallel. Said method is not advantageous when all chambers must be controlled individually.

Before the chambers are sold, different reagents are placed into the chamber reservoirs which are then sealed. The sealing can be accomplished in different ways, for example by means of films or in some other air-tight manner. During the actual use, these reagents must be removed from the reservoirs and applied to the pipetting surface in a certain order. This is preferably accomplished by piercing the reservoir seal with the tip of the pipette using a conventional pipette arm and aspirating the reagent liquid into the tip of the pipette. The pipette is then transported to the pipetting surface and the liquid is released. Such pipetting platforms are obtainable in the usual manner and are pro-grammable as needed.

It is recommended that certain liquid chemicals (also referred to as auxiliary reagents) not be supplied by a pipetting method but, rather, via a pipeline system. These are the chemicals that are needed independently of the particular application, such as dewaxing chemicals or washing solutions. To be able to control each chamber individually, the chambers must be controllable, for example, either with the aid of a valve system or via a multiway valve.

The invention also relates to a device for wetting objects, particularly materials, with a liquid that may contain an analytical reagent or a substance that is to be isolated, with a system for carrying the specimen slide that is disposed at a distance from a platform so as to form an interspace between the platform and the specimen slide for receiving the liquid, and with a system for raising and lowering the specimen slide relative to the platform whereby, in the raised or lowered position of the specimen slide or in the raised or lowered position of the platform, the liquid can be introduced into the interspace and can be removed from the interspace, and whereby the liquid during the raising and lowering of the specimen slide or during the raising and lowering of the platform is distributed uniformly in the interspace between the platform surface and the underside of the specimen slide, and the specimen slide is raised and lowered on one of its sides and/or the platform is raised or lowered on one of its sides. In the described device, by specific raising or lowering of the specimen slide or by a corresponding lowering or raising of the platform, the liquid is introduced into the interspace between the specimen slide and the platform and is removed therefrom. When the specimen slide and the platform are at a distance from another or are swiveled relative to one another, the liquid can be introduced into the interspace between the platform and the specimen slide and removed therefrom. When the specimen slide and the platform are moved relative to one another, the introduced liquid is distributed uniformly in the interspace between the specimen slide and the platform.

The invention claimed is:

1. A device for wetting objects on a specimen slide with a liquid containing one of an analytical reagent and a substance to be isolated, the device comprising:
   a platform that is disposed a distance from said specimen slide; and
   an adjustment system that adjusts said distance between said specimen slide and said platform by angularly adjusting said specimen slide relative to said platform between a first position and a second position such that movement from the first position to the second position distributes the liquid over a predetermined area between said platform and said specimen slide; and
   a support system that selectively supports said specimen slide on a first side and that supports said specimen slide on a second side to enable adjustment of said first side of said specimen slide relative to said platform;
   wherein said support system includes a plurality of support features to support said specimen slide during adjustment of said specimen slide relative to said platform; and
   wherein said plurality of support features includes first and second support features that are disposed from one another at a distance that is smaller than a length of a side of said specimen slide.

2. A device for wetting objects on a specimen slide with a liquid containing one of an analytical reagent and a substance to be isolated, the device comprising:
   a platform that is disposed a distance from said specimen slide; and
   an adjustment system that adjusts said distance between said specimen slide and said platform by angularly adjusting said specimen slide relative to said platform between a first position and a second position such that movement from the first position to the second position distributes the liquid over a predetermined area between said platform and said specimen slide;
   wherein said adjustment system comprises at least one striker on which said specimen slide rests during adjustment and which is movable back and forth essentially vertical relative to said specimen slide.

3. A device for wetting objects on a specimen slide with a liquid containing one of an analytical reagent and a substance to be isolated, the device comprising:
   a platform that is disposed a distance from said specimen slide; and
   an adjustment system that adjusts said distance between said specimen slide and said platform by angularly adjusting said platform relative to said specimen slide between a first position and a second position such that movement from the first position to the second position distributes the liquid over a predetermined area between said platform and said specimen slide;
   wherein in a lowered position said specimen slide and said platform are disposed essentially parallel to one another.

4. A device for wetting objects on a specimen slide with a liquid containing one of an analytical reagent and a substance to be isolated, the device comprising:
   a platform that is disposed a distance from said specimen slide; and
   an adjustment system that adjusts said distance between said specimen slide and said platform by angularly adjusting said specimen slide relative to said platform between a first position and a second position such that movement from the first position to the second position distributes the liquid over a predetermined area between said platform and said specimen slide;

wherein said platform includes a plurality of support points that support said specimen slide in a lowered position.

5. The device according to claim 4 wherein two of said plurality of support points are disposed along a side of said specimen slide, which remains resting on said two support points during adjustment of said specimen slide relative to said platform.

6. The device according to claim 4 wherein one of said plurality of support points is disposed along a side of said specimen slide, which rests on said one support point when said specimen slide is in said lowered position.

7. A device for wetting objects on a specimen slide with a liquid containing one of an analytical reagent and a substance to be isolated, the device comprising:

a platform that is disposed a distance from said specimen slide;

an adjustment system that adjusts said distance between said specimen slide and said platform by angularly adjusting said platform relative to said specimen slide between a first position and a second position such that movement from the first position to the second position distributes the liquid over a predetermined area between said platform and said specimen slide; and two parallel tracks defining a surface of said platform therebetween.

8. The device according to claims 1 wherein an end of said platform that is disposed adjacent to said support system is contoured.

9. The device according to claim 1 wherein an end of said platform that is disposed adjacent to said support system includes at least one drain/aspiration hole.

10. The device according to claim 1 an end of said platform that is adjacent to said adjustment system is contoured.

11. A device for wetting objects on a specimen slide with a liquid containing one of an analytical reagent and a substance to be isolated, the device comprising:

a platform that is disposed a distance from said specimen slide;

an adjustment system that adjusts said distance between said specimen slide and said platform by angularly adjusting said specimen slide relative to said platform between a first position and a second position such that movement from the first position to the second position distributes the liquid over a predetermined area between said platform and said specimen slide; and a pipetting surface that is disposed at an end of said platform and that is at least partially covered by said specimen slide.

12. The device according to claim 11 wherein said pipetting surface is disposed below a surface of said platform.

13. The device according to claim 11 wherein said pipetting surface is disposed 0.3 to 0.5 mm below a surface of said platform.

14. The device according to claim 11 further comprising a step that is formed between said platform and said pipetting surface.

15. The device according to claim 11 wherein said pipetting surface is inclined toward said platform.

16. The device according to claim 11 further comprising at least one hole through said pipetting surface that enables transfer of said liquid.

17. A device for wetting objects on a specimen slide with a liquid containing one of an analytical reagent and a substance to be isolated, the device comprising:

a platform that is disposed a distance from said specimen slide; and an adjustment system that adjusts said distance between said specimen slide and said platform by angularly adjusting said platform relative to said specimen slide between a first position and a second position such that movement from the first position to the second position distributes the liquid over a predetermined area between said platform and said specimen slide;

wherein said platform is pivotally adjustable relative to a support system that carries said specimen slide.

18. The device according to claim 17 further comprising a hinge that enables pivoting of said platform between a raised position and a lowered position.

19. The device according to claim 17 further comprising a swiveling arm that enables said platform to pivot between a raised position and a lowered position.

20. The device according to claim 17 wherein said platform is disposed above said support system.

21. The device according to claim 17 further comprising a pipetting channel formed in a marginal region of said platform, through which said liquid can be applied to said specimen slide and removed from said specimen slide.

22. The device according to claim 17 wherein said support system includes two tracks on which edges of a long side of said specimen slide selectively rest.

23. A device for wetting objects on a specimen slide with a liquid containing one of an analytical reagent and a substance to be isolated, the device comprising:

a platform;

a support system that enables said specimen slide to be disposed at a distance from said platform to form an interspace between said platform and said specimen slide for receiving said liquid; and an adjustment system for relatively adjusting said specimen slide and said platform with respect to each other, wherein said liquid can be introduced into said interspace and removed from said interspace and wherein said liquid is uniformly distributed in said interspace between a platform surface and an underside of said specimen slide in response to angular adjustment of said specimen slide relative to said platform.

24. The device according to claim 23 wherein a side of said specimen slide is adjusted relative to said platform.

25. The device according to claim 23 wherein a side of said platform is adjusted relative to said specimen slide.

26. A method of wetting objects on a specimen slide with a liquid that contains one of an analytical reagent and a substance to be isolated, the method comprising:

providing a platform;

supporting a side of said specimen slide on a support system relative to said platform, the support system defining an axis about which the specimen slide pivots; and adjusting an angular position of said platform relative to said specimen slide from a first position to a second position to uniformly distribute said liquid between said platform and said specimen slide and from the second position to the first position to remove said liquid from between said specimen slide and said platform proximate the axis.

27. The method according to claim 26 wherein said angular position is adjustable through 1° to 25°.

28. The method according to claim 27 wherein said angular position is adjustable through 8° to 10°.

* * * * *